United States Patent [19]

Money et al.

[11] 4,448,196

[45] May 15, 1984

[54] DELTA MODULATOR FOR MEASURING VOLTAGE LEVELS IN A HEART PACER

[75] Inventors: David K. Money, Pennant Hills; Tibor A. Nappholz, Drummoyne, both of Australia

[73] Assignee: Telectronics Pty. Ltd., Lane Cove, Australia

[21] Appl. No.: 393,801

[22] Filed: Jun. 30, 1982

[51] Int. Cl.³ .............................................. A61N 1/36
[52] U.S. Cl. .............................. 128/419 PT; 128/697
[58] Field of Search ........... 128/697, 419 PT, 419 PG

[56] References Cited

U.S. PATENT DOCUMENTS

| | | | |
|---|---|---|---|
| 3,689,879 | 9/1972 | Burdick | 128/419 PT |
| 3,782,367 | 1/1974 | Hochberg et al. | 128/419 PT |
| 3,841,336 | 10/1974 | Daynard | 128/419 PT |
| 3,923,041 | 12/1975 | Stasz et al. | 128/697 |
| 4,142,533 | 3/1979 | Brownlee et al. | 128/419 PT |
| 4,281,664 | 8/1981 | Duggan | 128/419 PT |
| 4,388,927 | 6/1983 | Schober | 128/419 PG |

Primary Examiner—William E. Kamm
Attorney, Agent, or Firm—Gottlieb, Rackman & Reisman

[57] ABSTRACT

A delta modulator for a heart pacer which not only allows sensed signals to be monitored, but also facilitates measurements of DC operating potential levels. The DC levels, and changes in them, can be measured accurately by equilibrating the modulator with the application to it of a suitable reference potential as the initial step in a measurement sequence. This same technique allows small signal variations to be tracked even if they are superimposed on large signals.

30 Claims, 5 Drawing Figures

DELTA MODULATOR FOR MEASURING VOLTAGE LEVELS IN A HEART PACER

DESCRIPTION

This invention relates to delta modulators for processing internal physiological signals sensed by an implantable medical prosthesis, and more particularly to the additional use of delta modulator for measuring operating potential levels in the prosthesis.

In the copending application of Money et al entitled "Time-Domain Processing of Internal Physiological Signals", Ser. No. 320,338 filed on Nov. 12, 1981, which application is hereby incorporated by reference, there is disclosed a delta modulator which allows timedomain processing of internal physiological signals. The use of such a modulator permits digital processing of analog physiological signals, even in the input stage of a heart pacer, for example, rather than conventional frequency-domain processing. The input signal is converted to a bit stream which, in addition to being operated upon within the pacer, can be transmitted to an external monitor; the bit stream can be used to form an accurate reconstruction of the sensed signal.

The delta modulator disclosed in said copending application in effect tracks the analog signal being monitored. A continuous sequence of bit samples is generated, the two states of the bit samples representing changes in respective opposite directions in the sensed signal. If the input signal starts to change in one direction, a sequence of bits of one value will be generated by the delta modulator; a change in the input signal in the opposite direction causes a sequence of bits of opposite value to be generated. The input signal which is operated upon by the delta modulator can be reconstructed by causing a fixed-size step to be taken for each received bit sample, the direction of the step depending upon the bit-sample value. Once the input signal settles down to a quiescent level, and after the delta modulator has caught up to the input signal, bit samples of alternating values are generated. An excess of bit samples of the same value are then generated only after the input signal starts to change. As long as the delta modulator operates at a fast enough rate, the reconstructed signal will accurately follow the input signal.

While a delta modulator offers numerous advantages insofar as the monitoring of analog signals is concerned, it is also important to monitor DC operating potentials at various points in the circuitry of an implanted prosthesis. Preferably, data representing the monitored potential levels should be transmitted externally of the patient so that the various potential levels may be ascertained by an external monitor. Typically, depending upon pacer characteristics, for example, the physician may appropriately program the pacer operation. Heretofore, however, to the extent that potential levels in a medical prosthesis could be monitored and transmitted externally, separate circuits were required for this purpose.

It is a general object of our invention to enable the same delta modulator circuit which is capable of monitoring and transmitting sensed physiological signals to also control measurements of DC levels.

One of the problems in using a delta modulator to monitor analog signals is that the accuracy of the device is proportional to the amplitude of any change in the input signal. It is often desirable to monitor a small-varying signal which is superimposed on a large one. For example, in a heart pacer it would be highly advantageous to monitor the decrease in pulse amplitude between the leading and trailing edges of the pacing pulse; the slope of the decreasing amplitude is a measure of the electrode impedance. However, a conventional delta modulator cannot generate a bit sequence from which this small-varying signal which is superimposed on the large-amplitude pacing pulse can be reconstructed because the accuracy of the modulator is a function of the overall pulse amplitude. For example, if the pacing pulse has an amplitude of about 8 volts and the accuracy of the delta modulator is 2%, the accuracy of any reconstructed pacing pulse signal is limited to about 0.16 volts. But the entire change in pacing pulse amplitude between the leading and trailing edges may be in the order of 100 millivolts; thus it is apparent that reconstruction of the pacing pulse waveform from the bit sample sequence generated by the delta modulator will not allow the slope of the pulse to be determined with any meaningful degree of accuracy.

It is another object of our invention to allow a delta modulator to generate a bit sample sequence from which there can be reconstructed accurately small-varying signal components which are superimposed on large signal components.

Briefly, in accordance with the principles of our invention, the delta modulator used to monitor an analog physiological signal can also be used to control the measurement of a DC potential. The DC potential to be measured is first sampled. The sampled potential is then applied to the input of the delta modulator. Prior to application of the sampled potential to the input of the modulator, the modulator is allowed to equilibrate so that it generates bit samples of alternating values. Once the sampled potential is applied to the input, a sequence of bit samples of the same value is generated until the modulator equilibrates once again, at which time the generated samples have alternating values. Consequently, the number of samples of the same value which are generated in sequence represents a measure of the DC potential.

The modulator is initially equilibrated by applying a reference potential at its input. When the sampled DC potential is then applied, the step change at the input results in the generation of a number of bit samples of the same value which is proportional to the difference between the reference potential used for equilibration and the sampled potential. If the sampled potential is initially taken relative to the same reference level, the resulting measurement will be of the potential level of interest relative to the reference.

This same technique of equilibrating the delta modulator prior to the taking of a DC level measurement is the key to monitoring a small-varying analog signal which is superimposed on a large signal.

Further objects, features and advantages of our invention will become apparent upon consideration of the following detailed description in conjunction with the drawing, in which.

Figure 1:
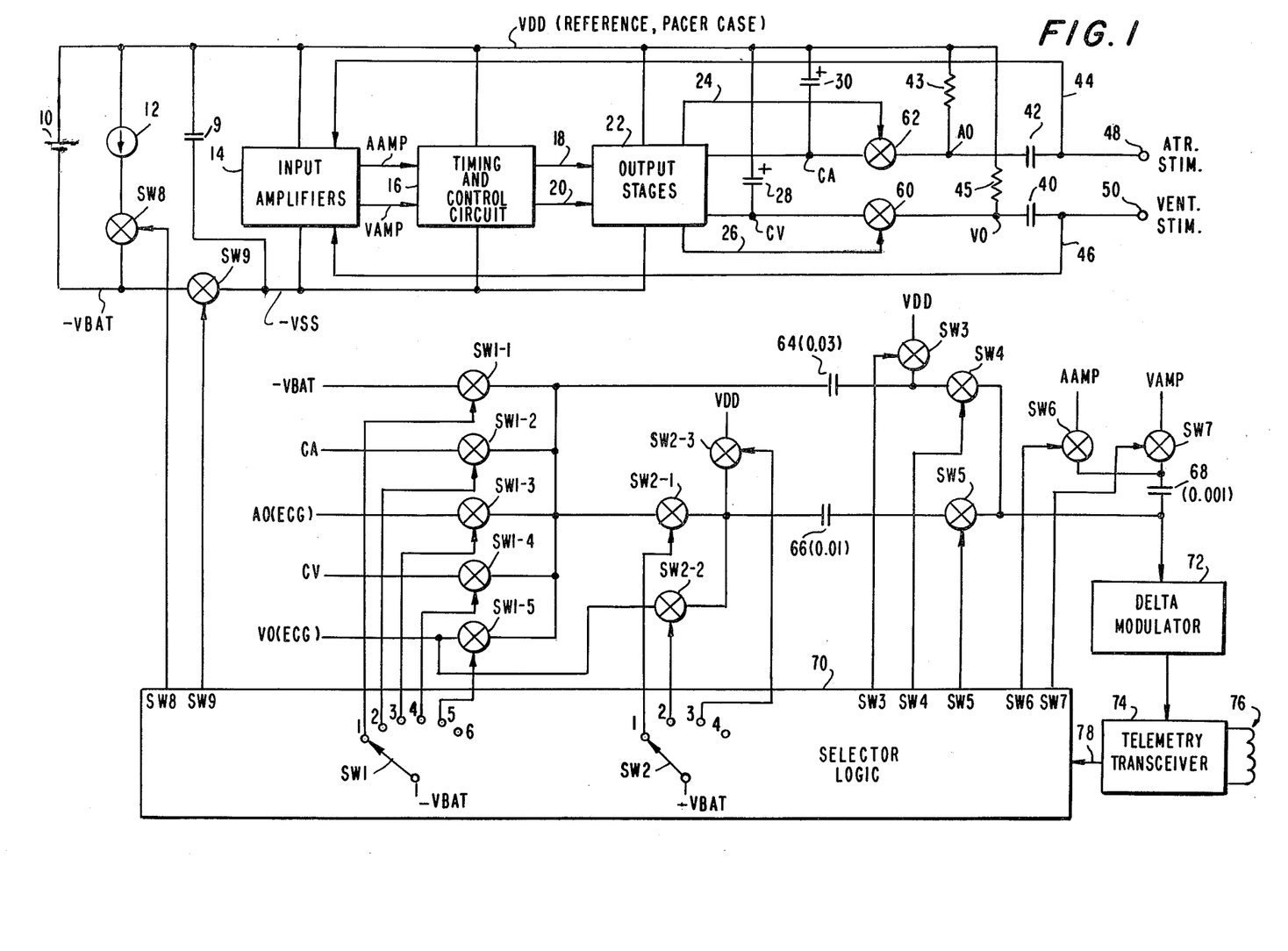
FIG. 1 depicts schematically the illustrative embodiment of our invention, in the form of a heart pacer.

Inasmuch as the present invention is concerned with how a sensed physiological signal may be monitored, and how the same circuitry which performs this task can also be used to monitor DC and other signals, the details of a particular implantable medical prosthesis are not required for an understanding of the invention. For this reason, FIG. 1 depicts an illustrative heart pacer in a very broad way; : the emphasis is on typical signals which may be monitored and measured, and the manner in which this is accomplished.

The heart pacer includes a powering battery 10, the positive terminal of which is connected to the metallic pacer case and serves as the reference potential VDD. The negative terminal of the battery is at a potential of −VBAT. Switch SW9 is ordinarily closed, and a negative potential −VSS serves to power the three operative subsystems of the pacer, these sub-systems being labelled by the numerals 14, 16 and 22. The magnitude of the −VSS potential is only slightly less than that of the −VBAT potential due to the drop across switch SW9. (All switches in FIG. 1 are CMOS analog switches which introduce minimal distortion.)

Atrial stimulating electrode 48 is coupled via conductor 44 to one of input amplifiers 14, and ventricular stimulating electrode 50 is coupled via conductor 46 to the other input amplifier. The input amplifiers amplify the sensed physiological signals to develop two amplified signals AAMP and VAMP, as shown in the drawing. The amplified sensed signals are applied to inputs of timing and control circuit 16. This circuit compares the amplified sensed signals with threshold values, and is responsible for the pacer timing and the triggering of stimulating pulses. When an atrial stimulating pulse is required, a trigger signal appears on conductor 18; when a ventricular stimulating pulse is required, a trigger signal appears on conductor 20.

Each of the two output stages in block 22 serves two functions. First, it controls the storage of charge on a respective one of capacitors 28, 30. Second, it controls the closing of a respective one of switches 60, 62 so that the stored charge may be delivered through a respective standard coupling capacitor 40, 42 to a respective one of the stimulating electrodes. Following the generation of an atrial stimulating pulse, when switch 62 is opened, the output stage associated with capacitor 30 controls a current flow through the capacitor, the capacitor charging with the polarity shown. The potential at node CA, relative to reference potential VDD, represents the magnitude of the voltage across capacitor 30. When an atrial stimulating pulse is required and conductor 24 is energized, switch 62 closes and charge from capacitor 30 flows through the switch, coupling capacitor 42, the atrial stimulating electrode, and body tissue to the grounded pacer case. After switch 62 opens once again at the end of the pacing pulse, capacitor 42 is re-charged through resistor 43, as is known in the art. Similar remarks apply to capacitors 28 and 40, switch 60, conductor 26, resistor 45 and node CV.

The signals at nodes AO and VO, if monitored, allow the shape of each type of stimulating pulse to be determined. Similarly, with large-magnitude capacitors 40, 42, the AO and VO signals represent the physiological signals on the atrial and ventricular electrodes which are of interest. (The signals are referred to as the "ECG" signals, although they are really "electrogram" signals as opposed to what is usually termed electrocardiographic signals.)

Figure 5:
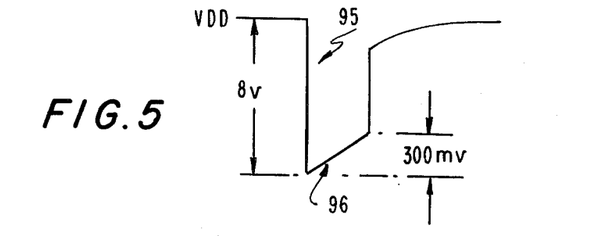
FIG. 5 depicts a typical heart pacer pulse which will be helpful in understanding certain aspects of our invention.

FIG. 5 depicts the shape of a typical ventricular pacing pulse. The VO node is initially at the reference potential VDD. When switch 60 closes and the negative potential CV is extended through switch 60, the VO potential drops sharply. (The drop is equal to the magnitude of potential CV, less the small drop across switch 60.) Typically, the VO node drops by around 8 volts at the start of the pacing pulse. As capacitor 28 then discharges through capacitor 40 and the ventricular stimulating electrode, the potential at the VO node decreases in magnitude. Segment 96 of the overall pacing pulse 95 in FIG. 5 corresponds to the discharge of capacitor 28. The magnitude of the decrease in the potential at the VO node during the discharge is in the order of 300 millivolts, as shown in the drawing. After switch 60 opens at the end of the pulse, the potential at node VO rapidly rises towards the reference potential VDD.

An important characteristic of the pacing pulse is the slope of line segment 96. The rate at which capacitor 28 discharges during generation of the pulse is a function of the electrode impedance. Thus the potential change from the start of the pulse to its termination, typically in the order of 300 millivolts, is one of the important quantities which must be measured. One of the difficulties in monitoring a signal such as that at the VO or AO node, with the use of a delta modulator, for example, is that the accuracy of the measurement is a percentage of the overall amplitude of the change at the input of the modulator. Suppose that the accuracy is 2% and the amplitude of the pulse is 8 volts, as shown. Measurements are thus accurate to only 160 millivolts, and the error is actually greater than the total amplitude of the small-varying signal of interest. Thus straight-forward monitoring of the VO signal cannot provide an accurate indication of the potential drop along line segment 96, from which the electrode impedance could be determined.

Another parameter of interest is the battery impedance. One way to determine the battery impedance is to open switch SW9 and to close switch SW8 for a brief interval. When the two switches are operated in this manner, the current from constant current source 12 flows through battery 10 and the −VBAT potential decreases in magnitude. The change in the −VBAT potential as the switches are switched is an indication of the battery impedance.

All measurements are controlled by selector logic 70 in FIG. 1. The selector logic extends control signals to numerous switches in the pacer for opening and closing them in particular sequences. Outputs SW8 and SW9 from the selector logic control the two similarly-labelled switches. Ordinarily, switch SW8 is open and switch SW9 is closed. By changing the states of the two switches as described immediately above, and by measuring the change in the −VBAT potential, the battery impedance can be determined. (For convenience, any output of the selector logic may be considered to close the respective switch when it is at the negative −VBAT level, the switch being open when the respective selector logic output is at the reference level VDD.)

The five switches SW1-1 through SW1-5 have connected to their respective inputs five signals which may be monitored. As shown in FIG. 1, these five signals are −VBAT, CA, AO, CV and VO. The AO and VO signals are also indicated as representing atrial and ventricular "ECG" signals, the two sensed physiological signals of interest as described above. Selector switch SWI is shown only symbolically as connecting the −VBAT potential to one of six possible outputs of the selector logic. When the switch is in position 1 switch SW1-1 is closed, when the switch is in position 2 switch SW1-2 is closed, etc. When selector switch SW1 is in position 6, none of switches SW1-1 thruogh SW1-5 is closed. A single selector switch SW1 is shown to indicate that at most only one of switches SW1-1 through SW1-5 is closed at any given time.

In a similar manner, selector switch SW2 can control one of switches SW2-1 through SW2-3 to be closed. At any given time, at most one of these switches is closed; all of them are open when the selector switch SW2 is in its "inoperative" position.

Outputs SW3 through SW7 of the selector logic control respective switches SW3 through SW7. The function of each of these outputs will be described below. Switches SW6 and SW7 have connected to their inputs respective signals AAMP and VAMP, the last two signals of interest which may be monitored in the system illustrated.

The monitoring circuit includes three capacitors 64, 66 and 68. Each of these capacitors is of a different magnitude (0.03, 0.01 and 0.001 microfarads respectively) for reasons which will be discussed below. Delta modulator 72 generates a continuous sequence of bit samples at its output, the two states of which represent changes in respective opposite directions in the signal at the input of the device. The delta modulator itself can take many forms, a preferred form being that shown in the above-identified Money et al application. For an understanding of the present invention, however, the details of the delta modulator are not required although certain aspects of its operation will be discussed shortly. The output of the delta modulator is extended to telemetry transceiver 74. The telemetry transceiver generates a signal across coil 76 which is transmitted to an external monitor. The transmitted signal represents the bit sequence at the output of the delta modulator. The telemetry transceiver also serves to sense externally-controlled signals which appear cross the coil for controlling the operation of selector logic 70. The sensed signals are applied over conductor 78 to the selector logic for controlling the operations of respective switches.

Figure 4:
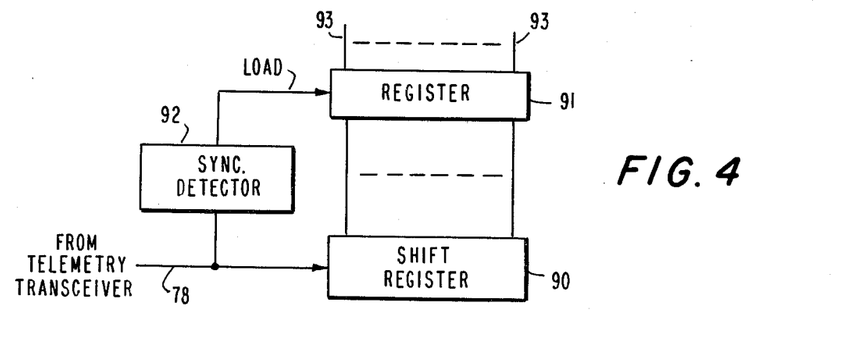
FIG. 4 depicts symbolically the manner in which the selector logic block 70 of FIG. 1 can be controlled.

The details of the telemetry transceiver and the associated external monitor/controller are also not important for an understanding of the present invention; such systems are well known in the art. The block diagram of FIG. 4 depicts the manner in which the selector logic outputs can be controlled by a bit sequence transmitted from an external control system. Referring to FIG. 1, it will be noted that the selector logic has fifteen outputs. The telemetry transceiver may therefore apply a fifteen-bit sequence to the input of the selector logic, as indicated in FIG. 4. The selector logic includes a shift register 90 into which the fifteen bits are shifted. A sync detector 92 determines when a fifteen-bit sequence has been received. (Although not indicated, certain check bits may also be applied in order that the selector logic determine that a valid sequence has been received, as is known in the art.) As soon as the sync detector determines that a fifteen-bit control sequence appears in shift register 90, it pulses the load input of register 91. At this time, the bits stored in the shift register are all loaded in respective stages of register 91. The outputs 93 of register 91 represent the fifteen control signals shown at the outputs of selector logic 70 in FIG. 1. The block diagram of FIG. 4 is included simply to illustrate one possible general form of control. What is important for an understanding of the present invention is the sequence in which the various switches are opened and closed, as will be described below.

Figure 3:
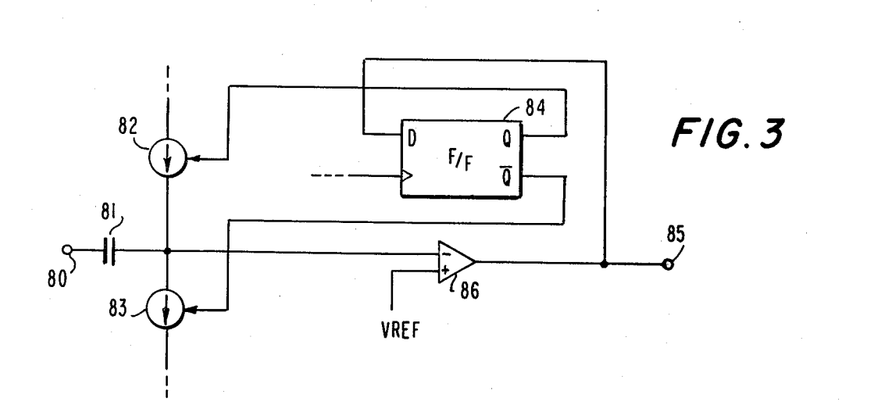
FIG. 3 depicts symbolically the principles of delta modulation described in detail in the aforesaid Money et al application.

It is important for an understanding of the present invention to appreciate the manner in which a delta modulator operates, and in this regard reference should be made to the symbolic block diagram of FIG. 3. An input analog signal appears at terminal 80, and a bit sequence output appears at terminal 85. The input signal is coupled through capacitor 81 to the minus input of comparator 86. A reference potential VREF is applied to the plus input of the comparator. Suppose, for example, that the input signal starts to decrease from some quiescent level. This tends to cause the potential at the minus input of the comparator to fall, and the output of the comparator goes high to indicate a bit value of 1. This, in turn, causes current source 82 to control a current flow from right to left through capacitor 81, tending to restore the potential at the minus input of the comparator to the reference potential. In a similar manner, current source 83 is operated to control a left-to-right current flow through capacitor 81 when the input signal increases from a quiescent level. The control of the current sources is shown symbolically by flip-flop 84. The output of the comparator is connected to the D input. The clock input is pulsed periodically to control the state of the flip-flop in accordance with the current bit sample. Since the two outputs of the flip-flop control operations of respective current sources, it is apparent that the output of the comparator not only represent a bit sample indicative of the manner in which the input signal is changing, but it also controls the current sources as required. In the case of a constant input, alternating 0 and 1 bit values appear at the output.

The delta modulator does not function to cause the potential at the minus input of the comparator to track that at input terminal 80. The comparator input is a virtual ground. What happens is that capacitor 81 is charged and discharged by the current sources so that the potential at input terminal 80 has added to it or subtracted from it a capacitor potential such that the resulting level at the minus input of the comparator equals the reference potential. If a steady-state condition has been achieved, with alternating 0 and 1 bit samples appearing at output terminal 85, and then there is a sudden change in the potential at input terminal 80, a number of bit samples of the same value will be generated until capacitor 81 has charged or discharged to an extent which compensates for the change at input terminal 80. The number of bit samples of constant value at the output of the delta modulator thus represent the magnitude of the change at input terminal 80, with the value of the output bits representing the direction of the change.

If a continuously changing input signal at terminal 80 is being monitored, the bit sequence at the output of the delta modulator allows the input signal to be reconstructed. But if a DC potential is to be measured, the delta modulator should first be allowed to equilibrate; the potential at input terminal 80 should be constant with capacitor 81 allowed to charge or discharge to the point at which bit samples of alternating values appear at the output. When the DC level to be measured is then applied to the input terminal, the bit samples at the output will be of constant value until capacitor 81 has once again charged or discharged to a point at which the output bit samples once again alternate in value. The number of bit samples of constant value which are generated following application to the input terminal of the potential to be measured represents the difference between the potential at terminal 80 just prior to the measurement process and the potential at the terminal at the start of the measurement process. When dealing with the potential of a node, what is meant is the potential relative to some other potential. Thus pains should be taken to ensure that prior to the start of the measurement process, a particular reference potential is applied to input terminal 80 and the delta modulator allowed to equilibrate. Thereafter, when the potential of interest is suddenly applied to the input terminal, the number of bits of constant value which will be generated at the output will reflect the potential of the node to be measured relative to the particular reference potential initially applied.

Capacitor 81 in FIG. 3 is the input capacitor to the delta modulator. In the system of FIG. 1, delta modulator 72 does not include an input capacitor. Instead, one of capacitors 64, 66 or 68 serves as the input capacitor. Different-magnitude capacitors are used in order to measure changing signals of different magnitudes. Suppose, for example, that delta modulator 72 operates at a 16-kHz rate, and that the input capacitor is of a size such that during each clock period of the delta modulator one of the two current sources controls a step change across the capacitor of 0.3 millivolts. This means that the system is slew-rate limited to (16 kHz)(0.3 millivolts) or 4.8 volts per second. Since an ECG signal changes at a rate slower than about three volts per second, the delta modulator bit output sequence can track a changing input signal. Since the same current is applied to the input capacitor during each cycle of operation of the delta modulator, each voltage change across the capacitor varies inversely with the capacitor magnitude. Thus the larger the capacitor, the greater the sensitivity because small changes in the input signal can be recognized and followed. Capacitor 64 is the largest of the three capacitors and is therefore used as the input capacitor of the delta modulator when analog signals (atrial) of lowest amplitude are being monitored; the capacitor is designed to provide a step change of 0.1 millivolts during each clock period of the delta modulator. Capacitor 66 is used to monitor signals (ventricular) of intermediate amplitude, and capacitor 68 is used to monitor the largest amplitude signals (the amplified inputs AAMP and VAMP).

It should also be appreciated that telemetry transceiver 74 need not necessarily transmit to the external world the bit samples derived by the delta modulator at the 16-kHz rte; it may be difficult to transmit at such a high frequency through a metallic case due to eddy current effects. Instead, it is possible to form a running sum over 4 milliseconds of 64 bit samples at the output of the delta modulator, and to transmit only a 6-bit data value which represents the sum of the 64 bits. (Six bits are required to represent a decimal value in the range 0–63.) This allows the transmission rate to be reduced significantly. While the resolution of the signal which is reconstructed by an external monitor would in theory be affected, the data rate would still be sufficient to allow signals being monitored to be reconstructed with adequate resolution. As the level of heart pacer bhip integration increases in coming years, it is expected that circuitry in the pacer itself will analyze the delta modulator bit stream output and transmit to the external world signals indicative of the results. It is to be appreciated that our invention relates to how the delta modulator derives a bit sequence which can represent DC potentials to be measured as well as analog signals to be tracked, and the bit sequence itself can be operated upon either internally or by an external monitor.

When monitoring the atrial physiological signal which appears at node AO in FIG. 1, selector switch SW1 closes switch SW1-3, and selector logic 70 also closes selector switch SW4. Thus the atrial signal at electrode 48, which appears at node AO, is coupled through switches SW1-3 and SW4 to the input of the delta modulator, with the largest capacitor 64 serving as the input capacitor. This is as required for the low-magnitude atrial signal. The position of selector switch SW2 is of no moment since all of switches SW2-1 through SW2-3 have their outputs connected through capacitor 66 to the input of switch SW5, and this latter switch is held open. (Switches SW6 and SW7 are also held open.) The atrial signal can thus be monitored as described in the above-identified Money et al application. When monitoring the ventricular signal which appears at node VO, selector switch SW1 selects none of switches SW1-1 through SW1-5 for operation, and selector switch SW2 selects switch SW2-2. At this time, only switch SW5 of switches SW3-SW7 is closed. It is thus apparent that the ventricular ECG signal is transmitted through switch SW2-2, capacitor 66 and switch SW5 to the input of the delta modulator. The intermediate-magnitude capacitor is utilized because the ventricular signal is larger in magnitude than the atrial signal and less sensitivity is required.

Two capacitors 64, 66 are thus used not simply because different sensitivities are required. The use of two capacitors allows the atrial and ventricular signals to be monitored simultaneously, something which may be of considerable diagnostic value. At alternate four-millisecond intervals, for example, a control sequence may be transmitted from the external monitor to the pacer to cause the selector logic to energize a different one of the two sets of outputs just described. When each capacitor is not beng use for coupling its respective input signal to the delta modulator, it serves as a memory element with the previous charge stored in it not dissipating. Thus when it is once again connected to the input of the delta modulator, tracking of the respective signal may resume. During the previous four milliseconds, the input signal associated with the now switched-in capacitor has changed, and the delta modulator must "catch up". However, the clock rate of the delta modulator is so fast relative to the rate at which the input signals change that the modulator output exhibits a negligible delay. Switching the capacitors at 4-millisecond intervals correspond to a rate of 125 Hz for each of the channels. The frequency components of interest in the atrial and ventricular signals are primarily in the 20–30 Hz range. Thus the switching of the capacitors is fast enough so as to present no significant problem in reconstitution. It is the use of two switched capacitors in this way that permits both signals to be monitored simultaneously (independent of continuous pacer operation). Were only a single capacitor utilized, two signals could not be monitored stimultaneously because the potential across the capacitor at the start of the monitoring of one of the signals would necessarily reflect the level of the other signal.

Either one of the amplified atrial and ventricular signals AAMP and VAMP may be monitored continuously simply by closing one of switches SW6 or SW7, capacitor 68 serving as the input capacitor to the delta modulator in such a case. As mentioned above, when monitoring the amplified atrial or ventricular signal, the smallest magnitude capacitor is utilized because these two signals have the largest amplitudes and the lowest sensitivity is required.

Another continuous signal of interest is −VBAT; monitoring the battery potential on a continuous basis provides information about the supply ripple. To monitor the battery potential, switches SW1-1 and SW4 are closed, with capacitor 64 serving as the input capacitor of the delta modulator.

As an example of a DC measurement, consider once again the monitoring of the −VBAT potential. In this case, however, it is not desired to monitor the battery potential continuously so that the supply ripple can be followed; instead, the open-circuit magnitude of the battery potential relative to the reference potential VDD is desired at some particular instant. As mentioned above, in order to measure any DC potential relative to some reference, the delta modulator must first be allowed to equilibrate by coupling the reference level to the input of the modulator. Toward this end, switches SW2-3 and SW5 are first closed. The VDD reference potential is thus applied to the input of capacitor 66, it being this capacitor which is used to measure the open-circuit −VBAT potential. After the delta modulator has equilibrated, switch SW9 is opened and switches SW1-1 and SW3 are closed. Switch SW9 is opened so that the potential which is measured is that of the battery without the potential being decreased by current flowing through the battery (i.e., what is measured is the open-circuit potential). By closing switches SW1-1 and SW3, the VDD reference potential is applied to the right side of capacitor 64 and the −VBAT potential is applied to the left side of the capacitor; thus the potential across the capacitor is equal to the potential to be measured relative to the reference. The potential of interest is sampled by capacitor 64 because switch SW9 cannot be held open for the several seconds required by the delta modulator to effect the measurement since the pacer would be inoperative during this time. The time required to effect the measurement is inversely related to the resolution of the measurement. Thus switch SW9 is opened for only about one millisecond, a time sufficient to allow a sample of the potential of interest to be stored across capacitor 64, but a time sufficiently short so that turning off of the pacer can be tolerated. Another reason for the sampling is that DC operating levels are not necessarily constant; as capacitors 28 and 30 charge, for example, the current drain from the battery can affect the −VBAT level significantly. Since several seconds may be required for measurement until the delta modulator equilibrates once again, a direct measurement might not be possible if the potential of interest changes during the measurement interval. Both capacitors 64 and 66 are used to advantage —one to control initial equilibration and the other to store a sample.

After the sampling step, switch SW1-1 is opened along with the closing of switch SW9. At the same time switch SW2-3, which was previously closed to allow the delta modultor to equilibrate for a reference potential of VDD, opens once again and switch SW2-1 now closes. The net effect is that the potential at the left side of capacitor 66 suddenly increases from the initial VDD level to the potential at the left side of capacitor 64, this latter potential being equal to −VBAT (relative to the VDD reference level). During the next few seconds the delta modulator generates a sequence of bit samples of constant value. The number of such samples until the delta modulator starts to generate samples of alternating values is a measure of the −VBAT potential. At the end of the measurement, switches SW3, SW2-1 and SW5 may be opened. It is thus apparent that the use of a sampling technique allows the open-circuit battery potential to be determined without actually inhibiting operation of the pacer (by holding switch SW9 open) for the several seconds actually required for performing the measurement. (It should be noted that with capacitors 64 and 66 being connected in series during the measurement process the capacitance valve is decreased. Thus the result of the measurement must be scaled accordingly.

The same overall sequence can be used to measure the −VSS potential level (the closed-circuit battery potential, less a small drop across switch SW9), simply by not opening switch SW9 during the one-millisecond sampling interval. The external control system can determine when sampling is to take place by monitoring the continuous ECG signals as described above. For example, by monitoring the continuous signals it can be determined when pacing pulses are not being generated, and it is at this time that the −VSS potential might be sampled for measurement.

In order to measure the CA and CV potential levels, the sequence is similar to that employed for measuring the −VBAT level (although switch SW9 remains closed). The only difference is that during the sampling process, it is one of switches SW1-2 or SW1-4 which is closed, rather than switch SW1-1.

In order to measure the impedance of battery 10, as described above what is done is to cause current from source 12 to flow through the battery so that the magnitude of the −VBAT potential is decreased. The drop in the −VBAT potential is directly proportional to the battery impedance. However, if both −VBAT measurements are taken relative to the reference level, because the system error is a function of the step change at the input of the delta modulator, an accurate measurement of the change in potential may not be possible; the measurement error may actually exceed the difference in potential. For this reason, what is done is to allow the delta modulator to equilibrate for a −VBAT input at a time when switch SW8 is open. After the delta modulator equilibrates, switch SW8 is closed and switch SW9 is opened so that a sample of the −VBAT potential level may be taken when it is reduced by the drop across the battery caused by current source 12. It is this sample which is then applied as a step input to the delta modulator. Since the step change is now equal to the difference between the −VBAT level with and without current source 12 affecting the potential of the battery, the relatively small change in the battery potential may be measured accurately. It is the change in potential which is directly proportional to the battery impedance, and from which an accurate determination of the battery impedance may be made.

At the start of the sequence, switches SW1-1 and SW2-1 are closed so that the −VBAT potential (with switch SW8 open) is applied to the left side of capacitor 66. The delta modulator is allowed to equilibrate, that is, the external monitor waits until bit samples of alternating value are detected. At this time, selector switch SW2 is moved to its "inoperative" position, and the left side of capacitor 66 remains floating during the ensuing rapid sampling. Switch SW1-1 remains closed; but now switch SW9 is opened, and switches SW8 and SW3 are closed. With switch SW9 open and switch SW8 closed, the −VBAT potential is equal to the original level, less the drop caused by the product of the current source magnitude and the battery impedance. The new −VBAT level, referenced to VDD, is sampled and stored across capacitor 64. Therefter, switch SW8 is returned to its normal open state and switch SW9 is returned to its normal closed state. If switch SW1-1 is now opened and switch SW2-1 is now closed, it is apparent that the left side of capacitor 66 suddenly changes in potential in accordance with the charge stored in capacitor 64; the sudden change in potential is dependent upon the two −VBAT levels, and it is relatively small. The usual delta modulator measurement is thus of the change in the −VBAT level, which in turn allows the battery impedance to be determined. (Once the battery impedance is known, and after measurements of −VBAT are made with switch SW9 both open and closed, the supply current may be calculated if it is of interest.)

When thus measuring the battery impedance, as just described the controlling potential is referenced to the −VBAT level; however, because the initial equilibration takes place while switch SW9 is closed, equilibration occurs while the battery powers the pacer circuitry. Thus the measurement is slightly inaccurate in that the reference is not an open-circuit voltage, while the sample taken is the open-circuit voltage when switch SW8 is closed and switch SW9 is opened. The alternative, however, is to hold switch SW9 open during equilibration. This might take several seconds, and the drop in the −VSS potential, even with the provision of a conventional storage capacitor 9 across the battery, might result in the detection of an "end-of-life" condition with a resulting change in pacer operation if the pacer is designed to change its operation toward the end of life of the battery.

This basic technique of referencing delta modulator measurements to different potentials so that step inputs may be made smaller, thus allowing measurements of potential differences to be made without the inherent errors being excessive, may also be used to measure pacing pulse characteristics. This most important type of measurement will now be described with reference to the ventricular pacing pulse of FIG. 5.

The measurement sequence first calls for the closing of switches SW1-4 and SW2-1 so that the CV potential level appears at the input of capacitor 66; at the same time, switch SW5 is closed so that the delta modulator equilibrates for a CV input potential level. Shortly prior to the generation of the pacing pulse, selector switch SW2 is moved to its inoperative position so that switch SW2-1 opens; the left side of capacitor 66 remains floating. Subsequent to the pacing pulse, the CV voltage has dropped an amount related to the charge delivered into electrode 50. The new value is now sampled on capacitor 64 wirh switch SW3 closed. This sampling process takes a few milliseconds. Switch SW1-4 is now opened and switches SW2-1 and SW5 are closed. The change in CV voltage is thus applied to the delta modulator.

As there are two capacitors 28 and 40 in the ventricular output section, the voltage drop shown in FIG. 5 as 300 mv is twice the calculated value if the two capacitors are equal in magnitude. If the pacing pulse voltage is known, the electrode impedance may be calculated.

Pacing pulse amplitude may be measured as follows. With switch SW3 closed, switch SW2-3 is closed, switch SW2-1 is opened, and the delta modulator is equilibrated to potential VDD. A pacing pulse is then sampled on capacitor 64 via switch SW1-5. After switch SW1-5 is opened, capacitors 64 and 66 are then connected in the conventional fashion by opening switch SW2-3 and closing switch SW2-1.

Similar remarks apply to atrial channel measurements.

Figure 2:
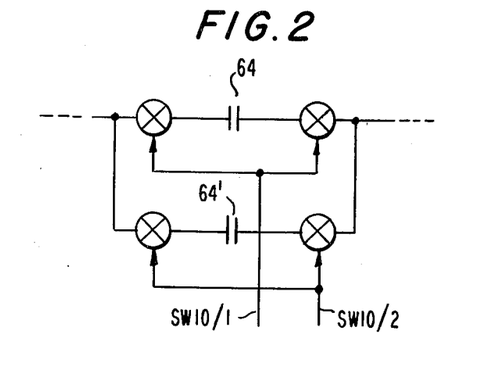
FIG. 2 depicts an add-on circuit for the system of FIG. 1 which allows the moisture content within the pacer case to be determined.

There is one further modification of the system depicted in FIG. 2; an additional two switches are connected on either side of capacitor 64, these two switches being controlled by additional output SW10/1 of selector logic 70. An additional capacitor 64' is also shown, this capacitor also having an additional pair of switches on either side of it, with these two switches being controlled by additional selector logic output SW10/2. Ordinarily, output SW10/1 is energized and output SW10/2 is not, so that capacitor 64 remains in the circuit and operates as described above. But if at any time output SW10/1 is de-energized and output SW10/2 is energized instead, capacitor 64' is inserted in the circuit instead of capacitor 64. Capacitor 64' is a moisture-sensitive capacitor. What is done is to perform a −VBAT measurement first with capacitor 64 in the circuit, and then to perform another −VBAT measurement with capacitor 64' in the circuit. Depending on the moisture content within the pacer case, the capacitance of capacitor 64' varies, and this in turn means that the voltage step size across capacitor 64' during each cycle of operation of the delta modulator is a function of the moisture content. By comparing the number of output bit samples of the same value required in the measurement of the −VBAT potential in the two cases, the relative step sizes can be determined. This, in turn, is an indication of the relative capacitance magnitudes, from which the moisture content can be determined. (Instead of measuring the −VBAT level, some other level could be measured in a comparable way; what is important are the numbers of bit samples of the same value required to complete the measurements when capacitors 64 and 64' are in the circuit, the relative numbers indicating by how much capacitor 64' has changed from its nominal value of 0.03 microfarads which in turn is an indication of moisture content.)

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An implantable medical prosthetic device having means for sensing a physiological signal to be monitored; and means for deriving from a sensed signal a continuous sequence of bit samples, an excess of one of the two states of said bit samples representing a change in a corresponding direction in the sensed signal; characterized by means for sampling an operating potential whose level is to be measured; and means for applying the sampled potential to the input of said bit-sample deriving means.

2. An implantable medical prosthetic device in accordance with claim 1 wherein said bit-sample deriving means derives bit samples of alternating states for a constant input after equilibration, and the level of the sampled potential is represented by the number of bit samples of the same state which are derived following application of the sampled potential to the input of said bit-sample deriving means after initial equilibration.

3. An implantable medical prosthetic device in accordance with claim 2 wherein the level of the sampled potential is to be measured relative to a reference potential, and further characterized by means for applying said reference potential to the input of said bit-sample deriving means for initial equilibration.

4. An implantable medical prosthetic device in accordance with claim 3 wherein said sampling means includes a first capacitor for representing the sampled potential, said reference potential applying means includes a second capacitor through which said reference potential is initially applied, and said sampled potential applying means connects said first capacitor to said second capacitor.

5. An implantable medical prosthetic device in accordance with claim 4 wherein said sampling means includes means for applying the potential whose level is to be measured to one side of said first capacitor while it applies said reference potential to the other side of said first capacitor.

6. An implantable medical prosthetic device in accordance with claim 3 wherein the prosthetic device includes a powering battery, and further characterized by means for selectively causing a constant current to flow through said battery while simultaneously inhibiting powering of the prosthesis by said battery, whereby equilibration by the powering potential of said battery and subsequent sampling of the battery potential while said constant current flows therethrough, followed by measurement of the sampled battery potential relative to said equilibration powering potential, enables the battery impedance to be determined from the measurement.

7. An implantable medical prosthetic device in accordance with claim 3 wherein the prosthetic device is a heart pacer and said sensing means senses the signal on a heart electrode, and said reference potential applying means controls said bit-sample deriving means to equilibrate for a reference potential equal to the amplitude of the leading edge of a pacing pulse.

8. An implantable medical prosthetic device in accordance with claim 3 wherein the prosthetic device is a dual-chamber heart pacer, and said sensing means is characterized by first means for sensing atrial signals to be monitored and second means for sensing ventricular signals to be monitored, each of said first and second sensing means including a respective capacitor for coupling the respective sensed signal to the input of said bit-sample deriving means, whereby alternate couplings of said capacitors in said first and second sensing means to the input of said bit-sample deriving means allows both of said sensed signals to be monitored simultaneously.

9. An implantable medical prosthetic device in accordance with claim 8 wherein the capacitor in said atrial sensing means is larger in magnitude than the capacitor in said ventricular sensing means.

10. An implantable medical prosthetic device in accordance with claim 3 further characterized by means for switching first and second capacitors in the input of said bit-sample deriving means, one of said first and second capacitors having a capacitance which varies with moisture content and said bit-sample deriving means operating as a delta modulator, whereby measurements of the level of the same potential with said first and second capacitors switched in allows the moisture content inside the prosthetic device to be determined from the relative numbers of bit samples of the same state which are derived during the two measurements.

11. An implantable medical prosthetic device in accordance with claim 1 wherein the level of the sampled potential is to be measured relative to a reference potential, and further characterized by means for applying said reference potential to the input of said bit-sample deriving means for initial equilibration prior to operation of said sampled potential applying means.

12. An implantable medical prosthetic device in accordance with claim 11 wherein said sampling means includes a first capacitor for representing the sampled potential, said reference potential applying means includes a second capacitor through which said reference potential is initially applied, and said sampled potential applying means connects said first capacitor to said second capacitor.

13. An implantable medical prosthetic device in accordance with claim 12 wherein said sampling means includes means for applying the potential whose level is to be measured to one side of said first capacitor while it applies said reference potential to the other side of said first capacitor.

14. An implantable medical prosthetic device in accordance with claim 1 wherein said prosthetic device includes a powering battery, and further characterized by means for selectively causing a constant current to flow through said battery while simultaneously inhibiting powering of the prosthetic device by said battery, whereby initial equilibration of said bit-sample deriving means by the powering potential of said battery and subsequent sampling of the battery potential while said constant current flows therethrough, followed by measurement of the sampled battery potential relative to said equilibration powering potential, enables the battery impedance to be determined from the measurement.

15. An implantable medical prosthetic device in accordance with claim 1 wherein the prosthetice device is a heart pacer and said sensing means senses the signal on a heart electrode, and said reference potential applying means controls said bit-sample deriving means to equilibrate for a reference potential equal to the amplitude of the leading edge of a pacing pulse.

16. An implantable medical prosthetic device in accordance with claim 1 wherein the prosthetic device is a dual-chamber heart pacer, and said sensing means is characterized by first means for sensing atrial signals to be monitored and second means for sensing ventricular signals to be monitored, each of said first and second sensing means including a respective capacitor for coupling the respective sensed signal to the input of said bit-sample deriving means, whereby alternate couplings of said capacitors in said first and second sensing means to the input of said bit-sample deriving means allows both of said sensed signals to be monitored simultaneously.

17. An implantable medical prosthetic device in accordance with claim 16 wherein the capacitor in said atrial sensing means is larger in magnitude than the capacitor in said ventricular sensing means.

18. An implantable medical prosthetic device in accordance with claim 1 further characterized by means for switching first and second capacitors in the input of said bit-sample deriving means, one of said first and second capacitors having a capacitance which varies with moisture content and said bit-sample deriving means operating as a delta modulator, whereby measurements of the level of the same potential with said first and second capacitors switched in allows the moisture content inside the prosthetic device to be determined from the relative numbers of bit samples of the same state which are derived during the two measurements.

19. An implantable medical prosthetic device having means for sensing a physiological signal to be monitored; and means for deriving from a sensed signal a continuous sequence of bit samples, an excess of one of the two states of said bit samples representing a change in a corresponding direction in the sensed signal with bit samples of alternating states being derived for a constant input after equilibration; characterized by means for applying to the input of said bit-sample deriving means an operating potential whose level is to be measured, the level of the operating potential being represented by the number of bit samples of the same state which are derived following application of the operating potential to the input of said bit-sample deriving means after initial equilibration.

20. An implantable medical prosthetic device in accordance with claim 19 wherein the level of the operating potential is to be measured relative to a reference potential, and further characterized by means for applying said reference potential to the input of said bit-sample deriving means for initial equilibration.

21. An implantable medical prosthetic device in accordance with claim 20 wherein the prosthetic device includes a powering battery, and further characterized by means for selectively causing a constant current to flow through said battery while simultaneously inhibiting powering of the prosthetic device by said battery, whereby equilibration of said bit-sample deriving means by the powering potential of said battery, and subsequent measurement of the battery potential with said constant current flowing therethrough relative to said equilibration powering potential, enables the battery impedance to be determined from the measurement.

22. An implantable medical prosthetic device in accordance with claim 20 wherein the prosthetic device is a heart pacer and said sensing means senses the signal on a heart electrode, and said reference potential applying means controls said bit-sample deriving means to equilibrate for a reference potential equal to the amplitude of the leading edge of a pacing pulse.

23. An implantable medical prosthetic device in accordance with claim 19 wherein the prosthetic device is a dual-chamber heart pacer, and said sensing means is characterized by first means for sensing atrial signals to be monitored and second means for sensing ventricular signals to be monitored, each of said first and second sensing means including a respective capacitor for coupling the respective sensed signal to the input of said bit-sample deriving means, whereby alternate couplings of said capacitors in said first and second sensing means to the input of said bit-sample deriving means allows both of said sensed signals to be monitored simultaneously.

24. An implantable medical prosthetic device in accordance with claim 23 wherein the capacitor in said atrial sensing means is larger in magnitude than the capacitor in said ventricular sensing means.

25. An implantable medical prosthetic device in accordance with claim 19 further characterized by means for switching first and second capacitors in the input of said bit-sample deriving means, one of said first and second capacitors having a capacitance which varies with moisture content and said bit-sample deriving means operating as a delta modulator, whereby measurements of the level of the same operating potential with said first and second capacitors switched in allows the moisture content inside the prosthetic device to be determined from the relative numbers of bit samples of the same state which are derived during the two measurements.

26. A system for facilitating the measurement of an operating potential in an implantable medical prosthetic device comprising means for deriving from an input signal a continuous sequence of bit samples, an excess of one of the two states of said bit samples representing a change in a corresponding direction in the input signal with bit samples of alternating states being derived for a constant input after equilibration, and means for applying to the input of said bit-sample deriving means an operating potential whose level is to be measured, the level of the operating potential being represented by the number of bit samples of the same state which are derived following application of the operating potential to the input of said bit-sample deriving means after initial equilibration.

27. A system in accordance with claim 26 wherein the level of the operating potential is to be measured relative to a reference potential, and further including means for applying said reference potential to the input of said bit-sample deriving means for initial equilibration.

28. A system in accordance with claim 27 wherein said prosthetic device includes a powering battery, and further including means for selectively causing a constant current to flow through said battery while simultaneously inhibiting powering of the prosthetic device by said battery, whereby equilibration of said bit-sample deriving means by the powering potential of said battery, and subsequent measurement of the battery potential with said constant current flowing therethrough relative to said equilibration powering potential, enables the battery impedance to be determined from the measurement.

29. A system in accordance with claim 27 further including means for switching first and second capacitors in the input of said bit-sample deriving means, one of said first and second capacitors having a capacitance which varies with moisture content and said bit-sample deriving means operating as a delta modulator, whereby measurements of the level of the same operating potential with said first and second capacitors switched in allows the moisture content inside the prosthetic device to be determined from the relative numbers of bit samples of the same state which are derived during the two measurements.

30. A system in accordance with claim 26 further including means for switching first and second capacitors in the input of said bit-sample deriving means, one of said first and second capacitors having a capacitance which varies with moisture content and said bit-sample deriving means operating as a delta modulator, whereby measurements of the level of the same operating potential with said first and second capacitors switched in allows the moisture content inside the prosthetic device to be determined from the relative numbers of bit samples of the same state which are derived during the two measurements.

* * * * *